(12) United States Patent
Scheidig et al.

(10) Patent No.: US 12,426,846 B2
(45) Date of Patent: Sep. 30, 2025

(54) METHOD FOR OPERATING AN X-RAY FACILITY, X-RAY FACILITY, COMPUTER PROGRAM AND ELECTRONICALLY-READABLE DATA MEDIUM

(71) Applicant: Siemens Healthineers AG, Forchheim (DE)

(72) Inventors: Fabian Scheidig, Baiersdorf (DE); Marcus Radicke, Veitsbronn (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/950,262

(22) Filed: Nov. 18, 2024

(65) Prior Publication Data

US 2025/0160782 A1    May 22, 2025

(30) Foreign Application Priority Data

Nov. 20, 2023  (DE) ..................... 10 2023 211 529.8

(51) Int. Cl.
| | |
|---|---|
| *H01J 35/06* | (2006.01) |
| *A61B 6/00* | (2006.01) |
| *A61B 6/50* | (2024.01) |
| *H01J 35/08* | (2006.01) |
| *A61B 6/40* | (2024.01) |

(52) U.S. Cl.
CPC ................ *A61B 6/54* (2013.01); *A61B 6/502* (2013.01); *H01J 35/08* (2013.01); *A61B 6/40* (2013.01)

(58) Field of Classification Search
CPC .... A61B 6/00; A61B 6/02; A61B 6/08; A61B 6/025; A61B 6/03; A61B 6/06; A61B 6/12; A61B 6/4021; A61B 6/4028; A61B 6/42; A61B 6/4494; A61B 6/54; A61B 6/542; A61B 6/545; A61B 6/547; A61B 6/548

See application file for complete search history.

(56) References Cited

U.S. PATENT DOCUMENTS 4,991,189 A * 2/1991 Boomgaarden ...... A61B 6/5258
378/19

FOREIGN PATENT DOCUMENTS

| | | |
|---|---|---|
| DE | 102011083416 A1 | 3/2013 |
| DE | 102017203932 A1 | 9/2018 |
| WO | 2008/132635 A2 | 11/2008 |
| WO | 2009/110399 A1 | 9/2009 |

OTHER PUBLICATIONS

German Office Action and English translation for German Application No. 102023211529.8 mailed Jul. 4, 2024.

* cited by examiner

*Primary Examiner* — Don K Wong
(74) *Attorney, Agent, or Firm* — Harness, Dickey & Pierce, P.L.C.

(57) ABSTRACT

One or more example embodiments relates to a method for operating an x-ray facility, having an x-ray emitter arrangement with an x-ray emitter for sending out an x-ray field for examination of an examination object and an x-ray detector for receipt of x-ray radiation of the x-ray field, wherein the x-ray emitter arrangement has a mono tank for the x-ray emitter with a housing in which a radiation exit window for the x-ray radiation generated by the x-ray emitter is arranged, and a beam-forming facility for setting a desired extent and position of the x-ray field.

16 Claims, 3 Drawing Sheets

METHOD FOR OPERATING AN X-RAY FACILITY, X-RAY FACILITY, COMPUTER PROGRAM AND ELECTRONICALLY-READABLE DATA MEDIUM

CROSS-REFERENCE TO RELATED APPLICATION(S)

The present application claims priority under 35 U.S.C. § 119 to German Patent Application No. 10 2023 211 529.8, filed Nov. 20, 2023, the entire contents of which are incorporated herein by reference.

FIELD

One or more example embodiments relates to a method for operating an x-ray facility, having an x-ray emitter arrangement with an x-ray emitter for sending out an x-ray field for examination of an examination object and an x-ray detector for receiving x-ray radiation of the x-ray fields, wherein the x-ray emitter arrangement has a mono tank for the x-ray emitter with a housing, in which a radiation exit window for the x-ray radiation generated by the x-ray emitter is arranged, and a beam-forming facility for setting a desired extent and position of the x-ray field.

As well as this, one or more example embodiments relates to an x-ray facility, to a computer program and to an electronically readable data medium.

RELATED ART

X-ray facilities for imaging examination of a patient usually have an x-ray emitter for generation of x-ray radiation. In order to provide an x-ray field of a desired position and extent the x-ray emitter is usually assigned a beam-forming facility, which can be realized jointly with said emitter as a part of an x-ray emitter arrangement. Such a beam-forming facility can be a collimator and/or a diaphragm facility, for example. If the x-ray emitter is accommodated in a mono tank for example, which usually has a housing filled for example with a circulating cooling medium, in which the x-ray emitter is also arranged, which emits the x-ray radiation through a radiation exit window of the housing, the beam-forming facility can be attached to, in particular flanged onto, the mono tank, in particular in its own additional housing. The arrangement is then made so that diaphragms of the beam-forming facility (frequently also referred to as blades) act as required on the x-rays and, depending on the setting of the beam-forming facility, an x-ray field of a desired extent and position is produced.

In x-ray facilities for mammography (mammography facilities) the breast to be recorded as the examination object is for example supported directly or indirectly on the x-ray detector and is suitably compressed via what is known as a paddle, i.e. a compression plate, while the patient stands directly at the support arrangement comprising the compression plate and the x-ray detector. In this case the beam-forming facility can comprise a front diaphragm (front blade) and a rear diaphragm (rear blade), wherein the front diaphragm refers to the diaphragm provided facing towards the patient and the diaphragm provided facing away from the patient is referred to as the rear diaphragm. The x-ray field is to be adapted by appropriate activation of the beam-forming facility, i.e. positioning of the diaphragm, so that where possible the entire breast is recorded, but ideally as little radiation as possible directed towards the patient misses the x-ray detector. Limit values can be provided in this regard, for example.

During operation of the x-ray emitter via corresponding electrical power, the x-ray emitter heats up. If said emitter is embodied for example as an x-ray tube with a rotary anode supported in a vacuum via a carrier arrangement, power is also needed for a drive facility of the rotary anode, which can lead to a further heating up. This in its turn can lead to the rotary anode with the focal path shifting in relation to the x-ray facility as a whole, so that a shift in the focal spot, in other words focal point, relative to the beam-forming facility and/or to the x-ray detector can occur. Also, secondary effects, caused for example by the heating up of the housing of the mono tank can play a role. With a vacuum-supported rotary anode which is not directly bound to the coolant, this effect is especially strong, since the rotary anode and the carrier arrangement can only be poorly cooled in the cooling medium in the mono tank.

SUMMARY

Generally speaking, a shift in the x-ray field and thus in the irradiated region thereby occurs through thermal effects. Thus, the field of view can change during the examination, so that, in order to record the examination object, for example a breast, entirely, it would have to be set with certain safety margins in respect of the extent and position. In cases however in which x-ray radiation occurring outside the actual region to be recorded for imaging is undesirable, for example required maximum excess radiation times are present, this is a disadvantage however, in particular when such required maximum irradiation lengths, for example with mammography directed towards the patient, are reached or even exceeded.

One or more example embodiments provides a more reliable application of x-ray radiation in the field of view actually required.

This is achieved in accordance with a method, in particular a computer-implemented method, by an x-ray facility, by a computer program and by an electronically readable data medium in accordance with the independent claims. Advantageous developments emerge from the dependent claims.

BRIEF DESCRIPTION OF THE DRAWINGS

Advantages and details emerge from the exemplary embodiments described below, as well as with the aid of the drawings. In the figures.

DETAILED DESCRIPTION

Figure 1:
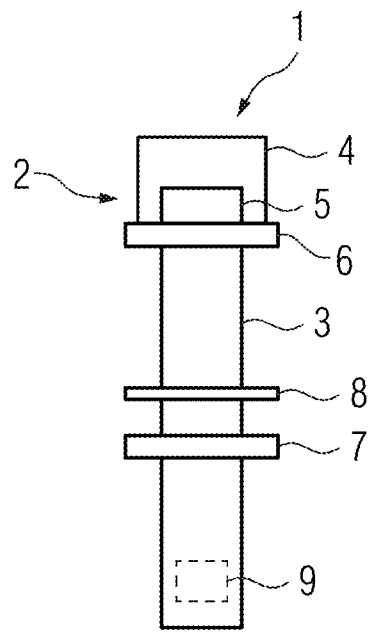
FIG. 1 shows a basic diagram of an inventive x-ray facility.

In a method of the type mentioned at the outset there is inventive provision, via a control facility of the x-ray facility, for discrepancy information, which describes a discrepancy caused by the temperature conditions in the x-ray emitter arrangement between the current extent and position of the x-ray field and the desired position and extent of x-ray field, to be determined, and for the beam-forming facility to be activated to at least partly compensate for the discrepancy, depending on the discrepancy information.

It is thus proposed to determine, directly or indirectly, temperature effects that lead to discrepancies, i.e. in particular to measure, estimate and/or directly establish discrepancies. Corresponding discrepancy information is then used in order to readjust the beam-forming facility accordingly and to obtain the desired extent and position of the x-ray field as accurately as possible, in particular to limit the x-ray field to the detector surface of the x-ray detector.

In particular and preferably the discrepancy information in this case relates to the relevant temperature conditions, in particular relevant temperatures, within the x-ray emitter, which can be measured and/or can be estimated from the known use of the x-ray emitter. This temperature information then present as discrepancy information, in particular at least one temperature value, can be used, by way of example, to calculate the position of the focal point, in particular focal spot, relative to the x-ray detector and the beam-forming facility and to readjust the beam-forming facility accordingly. Here, as will be explained in greater detail below, an explicit calculation of the position of the focal point is not undertaken directly, but it is also possible to use a discrepancy model, which outputs discrepancies or necessary correction measures directly.

In this way it is made possible to dispense largely or entirely with safety margins that may be too great as a result of thermal effects in the x-ray emitter arrangement and thus in particular on the one hand to ensure that the actually desired region is recorded and on the other hand that no unwanted x-ray radiation, in particular radiation that does not strike the x-ray detector, occurs. The radiation load for patients and/or other persons present can thus be reduced. No additional x-ray dose is applied by an incorrectly set x-ray field.

The use of the inventive procedure is especially advantageous when an x-ray tube with a rotary anode arranged rotatably via a carrier arrangement in a vacuum is used as the x-ray emitter. Such rotary anodes are not directly linked to a coolant, for example oil, and can therefore heat up along with their carrier arrangement, which can lead to relevant changes in position, in particular shifts, in the rotary anode, thus of the focal path and of the actual focal point. In this case the temperature of the rotary anode and/or of its carrier arrangement can be seen as relevant temperatures for example, which however can also be able to be determined indirectly, for example via a temperature in the mono tank.

In a first, advantageous embodiment of the present invention there can be provision for at least a part of the discrepancy information to be measured via at least one temperature sensor of the x-ray emitter arrangement. Here further temperatures, for example from a measured temperature distribution in the mono tank, at locations where they cannot be measured directly, can be derived as part of the discrepancy information. It is however especially expedient and for determination of more precise compensation measures, for relevant temperatures to be able to be measured directly. In the case of an x-ray tube with a rotary anode arranged rotatably in a vacuum for example, in a concrete embodiment of the invention provision can be made for the at least one temperature sensor, in particular embodied as an infrared sensor, to measure a temperature of the rotary anode and/or of the carrier arrangement. If the temperature sensor is embodied as an infrared sensor, it does not have to be arranged directly on the rotary anode and/or the carrier arrangement but can be directed towards these in order to detect the corresponding temperature.

There can further be provision in advantageous exemplary embodiments for at least one part of the discrepancy information to describe a power of the x-ray emitter that leads to a heating up, and/or to describe a cooling down period and/or to be determined from these variables. Since in the control facility, for example a corresponding recording unit for controlling the recording information, it is known when the x-ray emitter is being operated, x-ray radiation is thus being generated and/or the drive facility of the rotary anode is in operation, correspondingly applied powers and the periods of time for which these powers are acquired are known and can be employed as discrepancy information and/or to determine said information. Especially advantageously a power curve is determined that specifies both when (and ideally where) electrical power to operate the x-ray emitter will be applied and when cooling down periods lie between these phases, in which electrical power is applied. The applied power as well as the intervening cooling down periods primarily determine the temperature behavior of the x-ray emitter. Thus, an expedient development in this context makes provision, via a temperature model describing the heating up and cooling down behavior of the x-ray emitter, for a current temperature of the x-ray emitter, in particular of the rotary anode and/or its carrier arrangement, to be determined from the power and the cooling down period as discrepancy information. Temperature models, which in particular also describe the cooling down in cooling down periods are already known from other uses for x-ray emitters, in particular x-ray tubes, in the prior art, for example when it is a matter of estimating a possible throughput in x-ray facilities. Such temperature models, which describe both the heating up when power is applied and also the cooling down without any application of power and thus allow temperatures currently to be verified as an estimation, can expediently be employed in order to adjust the temperature conditions in the x-ray emitter constantly as current discrepancy information.

In a concrete embodiment of the present invention there can be provision for the discrepancy information to be used as input data for a discrepancy model delivering as output data at least one correction measure in accordance with which the beam-forming facility is activated. Such a discrepancy model can basically be an analytical model, which for example allows a shift in the focal point compared to the required position of the focal point to be determined as an internal intermediate result and to generate correction measures accordingly, in order through this shift to obtain discrepancies between the current extent and position of the x-ray field and the desired extent and position of the x-ray field. The discrepancy model can however also be at least partly empirical, as regards the shift in the focal point or directly the correction measures.

In general terms the discrepancy model delivers a link between the discrepancy information and the correction measures to be carried out, i.e. the readjustment. For example, the discrepancy model can thus contain a relationship between at least one relevant temperature and a way of readjusting at least one diaphragm. Here, in particular for empirical relationships, in which for example a function can be adapted to calibration data recorded in a calibration process still to be discussed, temperature values do not necessarily directly form input data, but the starting point can also be powers, in particular power curves with cooling down periods, and comparable variables, from which the temperature conditions follow indirectly. In particular it is also basically conceivable for the discrepancy model to comprise at least one trained function that has been trained by machine learning. Such a trained function can for example comprise a neural network, in particular a CNN, and be trained with the aid of calibration data as training data.

Thus, in a calibration process, values for the discrepancy information and assigned values for the discrepancies, thus correction measures, can be recorded and used in order to suitably adapt the discrepancy model. There can thus be provision for at least one parameter of the discrepancy model to be determined in a calibration process, in which discrepancies for various thermal states, described by respective discrepancy information of the x-ray emitter arrangement are measured. The calibration can in this case either be determined for the x-ray facility as a whole, for example for a type or a model of the x-ray facility, in particular with measurements at a number of different x-ray facilities; but it is also possible to carry out a specific calibration for a particular x-ray facility. Actually, a plurality of options exist for undertaking measurements that show the discrepancy.

In this case especially advantageously the measurement of the discrepancy relates to the position of at least one diaphragm of the beam-forming facility, as is imaged by the x-ray radiation. Such a position of a diaphragm represents a delimitation of the x-ray field. If it is now known where the diaphragm and thus the delimitation of the x-ray field should actually lie, an actual position of the diaphragm or delimitation of the x-ray field can be undertaken for a number of different thermal states, in other words temperature conditions, in the x-ray emitter arrangement, in particular the x-ray emitter, in order to determine suitable calibration data. For this it is basically conceivable to use an external measuring device; preferably however the x-ray detector and/or a measurement facility that forms part of the x-ray facility is employed.

In summary there can thus be provision for the at least one measured position of a diaphragm of the beam-forming facility (and thus of a delimitation of the x-ray field) for determining the discrepancy to be compared with a required position in accordance with activation of the beam-forming facility, in order to measure the discrepancy. Preferably the x-ray detector and/or a measurement facility permanently installed in the x-ray facility is used as the means for measuring the calibration process.

In concrete terms there can be provision for example, without a patient being present, for the diaphragm to be set so that its shadow falls on the x-ray detector, thus the delimitation of the x-ray field by the x-ray detector is acquired. Then the required position and actual measured position can be measured for various thermal states, in order to establish the discrepancy by comparing them. It is also possible to provide a measurement facility on one side next to the x-ray detector, with which, for diaphragm set to the edge of the x-ray detector, a discrepancy outward beyond the x-ray detector can also be measured and established. Such an additional measurement facility can preferably have a number of measurement chambers in order to obtain a spatial resolution.

In some situations, a discrepancy can actually be measured and used for updating the discrepancy model while the x-ray facility is in operation for an examination. In this way it is conceivable for example that, for updating the discrepancy model while in operation during an examination, at least one measurement facility to one side of the x-ray detector next to said detector and/or for an examination object not covering the entire x-ray detector, the x-ray detector is used for determining the position of a delimitation of the x-ray field (and thus measured position of a diaphragm). If not all of the x-ray detector is needed, for example in mammography with a small breast, the part of the x-ray detector not needed is shaded out via a diaphragm of the beam-forming facility. If it is now established that this shading is not being undertaken as required, i.e. the measured position of the delimitation of the x-ray field does not correspond to the required position, a discrepancy is established, which can be assigned to a current thermal state of the x-ray emitter arrangement, described by the discrepancy information. If in most cases the x-ray detector is fully used, the x-ray field is mostly also employed so that the x-ray detector is completely utilized, so that it can be expedient to use a permanently installed, additional measurement facility, which adjoins at least one side of the x-ray detector, in order also to measures the current position of a delimitation of the x-ray field beyond the extent of the x-ray detector. In order to provide a spatial resolution such a measurement facility can for example have a number of measurement chambers of an equal predefined extent following on from one another in the extension direction. In this way the measurement facility can be easily held yet still offer a spatial resolution.

In other forms of embodiment of the present invention it is however also possible to measure at least a part of the discrepancy directly and use it for deriving a correction measure. Then there can be provision for at least one part of the discrepancy information to be measured as a discrepancy between the location of a delimitation of the x-ray field and a required location in accordance with the desired position and extent of the x-ray field via the x-ray detector or by a measurement facility to one side of the x-ray detector and adjoining it. If for example the x-ray field is set so that, in the desired extent and position, it should entirely cover the x-ray detector, more precisely its detection surface, but if a shading out on one side is established on the recorded x-ray image, a (measured) discrepancy is present here, which can be taken into account for further x-ray recordings. If the discrepancy shifts to the other side, a measurement facility adjoining the x-ray detector as has already been described can be expedient for measuring this, in particular an embodiment with a number of measurement chambers in direction in which the measurement facility adjoins the x-ray detector. This is in particular expedient in respect of mammographic applications, since then for example the measurement can be made on the "rear" side, i.e. the side facing away from the patient and a correction measure for the "front" side, i.e. facing towards the patient can be derived from this. If there is no symmetry, the ray set can be used for example in order to determine discrepancies for other sides of the x-ray detector and this also correction measures in this regard. Since this type of "on the fly" calibration needs a first uncompensated image recording however, it is less preferred.

Overall, the procedure described here can also be used to particular advantage in mammography. A mammography facility can thus be used as the x-ray facility in which the beam-forming facility has a front diaphragm arranged facing towards the patient and a rear diaphragm arranged facing away from the patient, wherein at least the position of the front diaphragm is adapted for compensation for the discrepancy by activating the beam-forming facility. The front diaphragm is frequently also referred to here as the anterior blade or front blade, die rear diaphragm corresponding as the rear blade. It is precisely in mammography that even small discrepancies on the front side, i.e. facing towards the patient, can be extremely relevant, so that here a compensation is especially advantageous. If the x-ray field facing towards the patient deviates, radiation can be introduced into the patient that does not serve for imaging; this is unwanted. In this regard for example a maximum irradiation length already mentioned can also exists as a default. If on the other side the front delimitation of the x-ray field moves away from the patient, the breast may possibly not be captured entirely; this is also unwanted. Since discrepancies arising from thermal effects in the range of several millimeters have been observed, these are entirely relevant, and the inventive procedure can be employed especially advantageously in the field of mammography.

As well as the method, one or more example embodiments also relates to an x-ray facility, having an x-ray emitter arrangement with an x-ray emitter for sending out an x-ray field for examination of an examination object and an x-ray detector for receipt of x-ray radiation of the x-ray field, wherein the x-ray emitter arrangement has:
- a mono tank for the x-ray emitter with a housing in which a radiation exit window for the x-ray radiation generated by the x-ray emitter is arranged, and
- a beam-forming facility for setting a desired extent and position of the x-ray field, wherein the x-ray facility further has a control facility, which comprises:
- a determination unit for determining discrepancy information, which describes a discrepancy between the current extent and position of the x-ray field and the desired position and extent of the x-ray field caused by the temperature conditions in the x-ray emitter arrangement, and
- a compensation unit for activating the beam-forming facility to at least partly compensate for the discrepancy, depending on the discrepancy information.

In other words, the control facility is embodied for carrying out the inventive method. All that has been said with regard to the inventive method can be transferred by analogy to the inventive x-ray facility and vice versa, so that the advantages stated can also be obtained with said facility.

In particular the x-ray facility can for example have at least one temperature sensor and/or at least one measurement facility, which adjoins the x-ray detector in one direction. The control facility can comprise at least one processor and at least one memory module and has functional units formed by hardware and/or software, comprising the determination unit and the compensation unit. The control facility can also have further functional units, be they basically known functional units such as a recording unit for controlling the recording operation, or also functional units for realizing advantageous embodiments of the inventive method. The latter functional units can for example comprise a temperature model unit for application of a temperature model and/or a discrepancy model unit for application of the discrepancy model.

An inventive computer program is able to be loaded directly into a memory means of a control facility of an x-ray facility and has program means that, when the computer program is executed on the control facility, cause said facility to carry out the steps of an inventive method. The computer program can be stored on an electronically readable data medium in accordance with the present invention, which thus comprises control information stored thereon, which comprises at least one inventive computer program and is equipped in such a way that, when the data medium is used in a control facility of an x-ray facility, said facility is embodied to carry out an inventive method. The data medium can in particular involve a non-transient data medium, for example a CD-ROM.

FIG. 1 shows a schematic of an inventive x-ray facility 1, which is embodied in the present example as a mammography facility. In the following exemplary embodiments, the present invention is discussed with respect to an application case in the field of mammography.

The x-ray facility 1 comprises an x-ray emitter arrangement 2, which is mounted on a stand 3 and as well as a mono tank 4, in which an x-ray emitter 5 is arranged, also comprises a beam-forming facility 6, in the present example a collimator. Via a radiation exit window in the housing of the mono tank 4, not shown here in any greater detail, which for example faces towards the beam-forming facility 6 flanged onto the housing, and the beam-forming facility 6 an x-ray field of desired extent and position in relation to an x-ray detector 7 can be created. Above the x-ray detector 7, which also serves as a support for the breast to be recorded as the examination object, a compression plate 8 (paddle) is provided. The operation of the x-ray facility 1 is controlled by a control facility 9.

Figure 2:
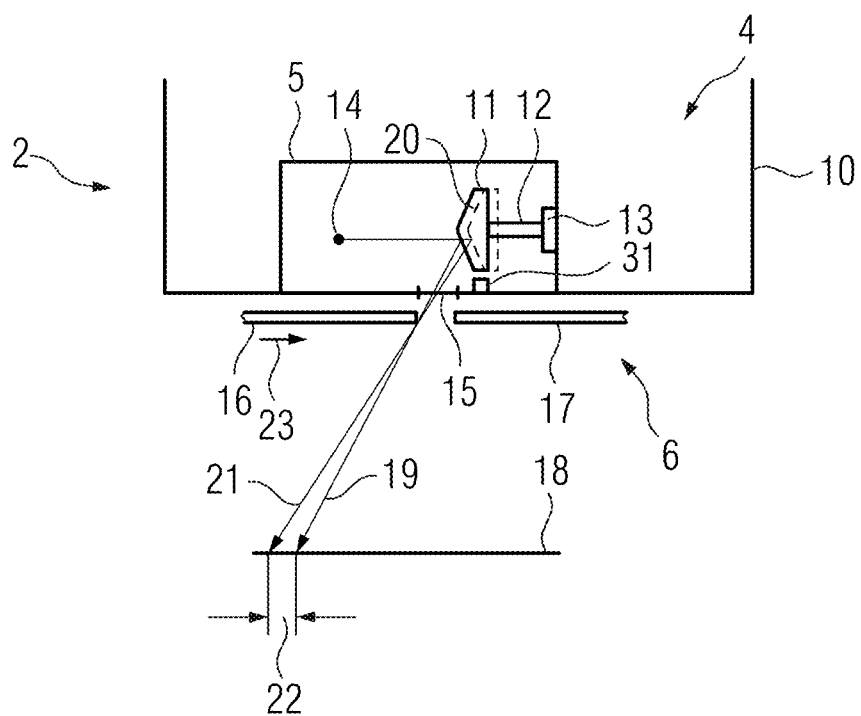
FIG. 2 shows a schematic diagram.

FIG. 2 shows the layout of the x-ray emitter arrangement 2 in relevant components in more detail. The x-ray emitter 5 arranged in the housing 10 of the mono tank 4 is embodied as an x-ray tube, which has a rotary anode 11, which in the present example is supported via a carrier arrangement 12 in a vacuum and is able to be rotated via a drive facility 13. A beam of electrons emitted by an electron source 14 only shown schematically strikes a focal path of the rotating rotary anode 11 and is converted there into x-ray radiation, which exits through the radiation exit window 15, for example a local thinning of the material of the housing 10. The beam-forming facility 6 comprises a front movable diaphragm 16, arranged facing towards the patient, thus in FIG. 1 outwards from the image plane, and a rear diaphragm 17, which for example can also be referred to as front blade and rear blade.

If the beam-forming facility 6 is set to a desired extent and position of the x-ray field, the rotary anode 11 is in a thermal reference state relative to the beam-forming facility 6 and to the x-ray detector 7 indicated here over the detector surface 18 relatively in the position shown by a solid line, at which an x-ray beam forming the front delimitation of the x-ray field, which can still just pass through the front diaphragm 16, is shown as arrow 19. Through thermal effects, depending on the temperature conditions, i.e. the thermal state, the result can be a shift in the rotary anode 11 into a shifted position 20 shown by a dashed line, so that the position is changed relative to the beam-forming facility 6 and to the x-ray detector 7. This leads to the delimitation of the x-ray field, indicated here in turn by an edge-side beam as arrow 21, likewise changing, thus producing a discrepancy 22 from the desired position of the delimitation of the x-ray field in accordance with the desired extent and position, which is unwanted. The procedure described here thus has the aim of analyzing the thermal state of the x-ray emitter 5 and determining at least one correction measure in order to compensate for this at least in part. A correction measure for the front diaphragm 16 is indicated in FIG. 2 by the arrow 23, a corresponding correction measure can, as the need arises, also be determined for the rear diaphragm 17.

Figure 3:
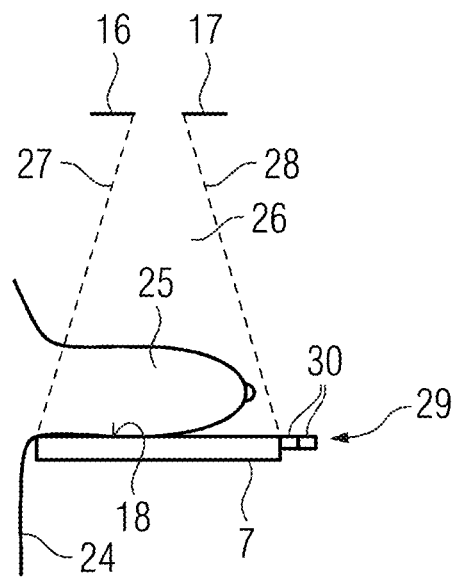
FIG. 3 shows an arrangement of an examination object for recording images.

FIG. 3 explains the situation in mammography once again in more detail. A patient 24 with a breast 25 to be examined is indicated, wherein for the sake of clarity the compression plate 8 is not shown. An optimal x-ray field 26 for this situation is shown and in the present example comprises exactly the breast 25 and the x-ray detector 7, in concrete terms its detector surface 18. If thermal effects now lead to a shift in the rotary anode 11, above all the front delimitation 27 of the x-ray field 26 is relevant, since here shifts in both directions are unwanted. Shifts in the delimitation 27 forwards, i.e. towards the patient 24, miss the detector 7 and represent an unnecessary radiation load. Shifts in the delimitation 27 backwards, i.e. away from the patient 24, lead to the breast 25 no longer being fully imaged. Therefore, correction measures in the present example comprise at least the corresponding adaptation of the position of the front diaphragm 16.

FIG. 3 also shows an option for how, in the context of a measurement, in particular with a small breast, but also for calibration of a discrepancy model, which is described in greater detail below, further information in respect of the rear delimitation 28 of the x-ray field 26 can be obtained. This certainly corresponds, like the front delimitation 27 in respect of the front diaphragm 16, to the shadowing of the rear diaphragm 17. If now, as a continuation of the detector surface 18 of the detector 7, a measurement facility 29 is connected to the rear of the x-ray detector 7, which for example, to establish a spatial resolution, can comprise a number of measurement chambers 30, a shift in the rear delimitation 28 in the rearwards direction can be verified, for example, since the measurement chambers 30 are correspondingly applied with x-ray radiation.

Figure 4:
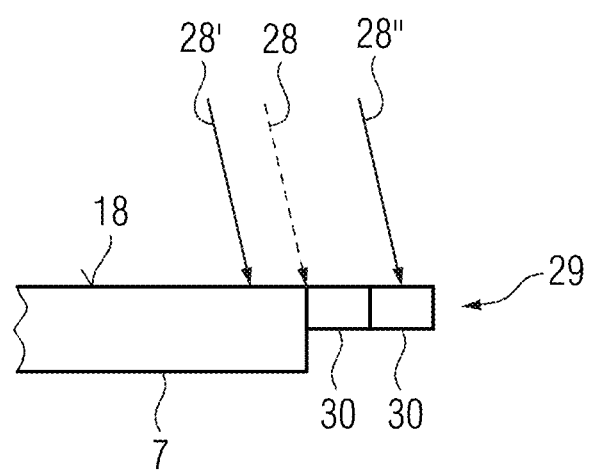
FIG. 4 shows a sketch to explain the use of a measurement facility.

One example of a measurement on the rear edge of the x-ray detector 7 is shown in FIG. 4, where, with a discrepancy from the required delimitation 28 forwards, the shadowing, deviating delimitation 28', can be seen on the x-ray detector 7, and with a shift backwards, deviating delimitation 28", measurement chambers 30 are applied with x-ray radiation applied and, in this way, show this shift. With mammography it is in particular conceivable to realize the inventive correction method to the extent that, via the x-ray detector 7 and optionally the measurement facility 29, a discrepancy arising from thermal effects between the location of the rear delimitation 28 and the required location is measured via the x-ray detector 7 and/or the further measurement facility 29 and accordingly from this a necessary correction measure in respect of the front diaphragm 16 is determined, with asymmetry by using the beam set.

Figure 5:
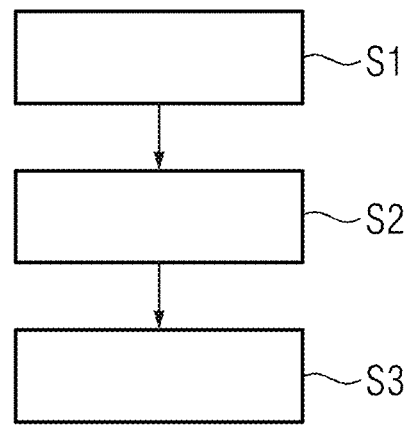
FIG. 5 shows a flowchart of an exemplary embodiment of the inventive method.

FIG. 5 shows a flowchart of another exemplary embodiment of the inventive method. In this example, in step S1, discrepancy information is determined, which in the present example in the form of at least one estimated and/or measured temperature, describes the temperature conditions in the x-ray emitter arrangement 2, in concrete terms for the rotary anode 11 and its carrier arrangement 12, i.e. the thermal state of relevant components of the x-ray emitter 5. Here it is possible on the one hand to measure the temperature of the rotary anode 11 and/or of the carrier arrangement 12 and also where necessary further temperatures via corresponding temperature sensors 31, cf. FIG. 2, wherein ideally infrared temperature sensors 31 are used within the x-ray emitter 5. It is also possible however for a derivation to take place from other temperature measurements; as an alternative or preferably in addition a temperature can also be obtained from the use of the x-ray emitter 5 known in the control facility 9. For this purpose, a power curve is provided which describes the power delivered in the periods of power for operation of the electron source 14 and the drive facility 13 as well as cooling down periods lying between them. Via a temperature model an estimated current temperature of the rotary anode 11 and/or of the carrier arrangement 12 can be determined from this and employed as discrepancy information.

In a step S2 the discrepancy information, in concrete terms the temperatures, is transferred to a discrepancy model as input data, which as output data delivers the discrepancies, which are able to be translated directly into correction measures, and/or the correction measures directly. This can involve an empirical, previously calibrated discrepancy model, but also an analytical discrepancy model, which for example can first calculate the shifted position of the focal point and can derive from this the discrepancies and necessary correction measures.

As already mentioned, the correction measures do not absolutely have to relate to all discrepancies of delimitations 27, 28, but in mammography for example can also just relate to the front diaphragm 16.

For calibration of such a discrepancy model, i.e. for determination of at least one parameter of the discrepancy model, a calibration process can be carried out. Here it is possible, for example by using the x-ray detector 7 alone, without an examination object, but also with additional use of the measurement facility 29, for various thermal states, described by discrepancy information, to measure discrepancies actually occurring, for example as a discrepancy between the location of delimitations 27, 28 and the required location. The resulting calibration data, in which discrepancy information is assigned to actual discrepancies, can be used for concrete parameterization of the discrepancy model, for example to fit a function of the discrepancy model and/or for machine learning of a trained function of the discrepancy model. If it is possible to measure discrepancies during examination operation, these can be employed for further optimization/plausibility checking of results of the discrepancy model.

Then, in a step S3 the correction measures, which result from the output data of the discrepancy model, are implemented accordingly, in that the control facility activates the beam-forming facility 6 accordingly.

Figure 6:
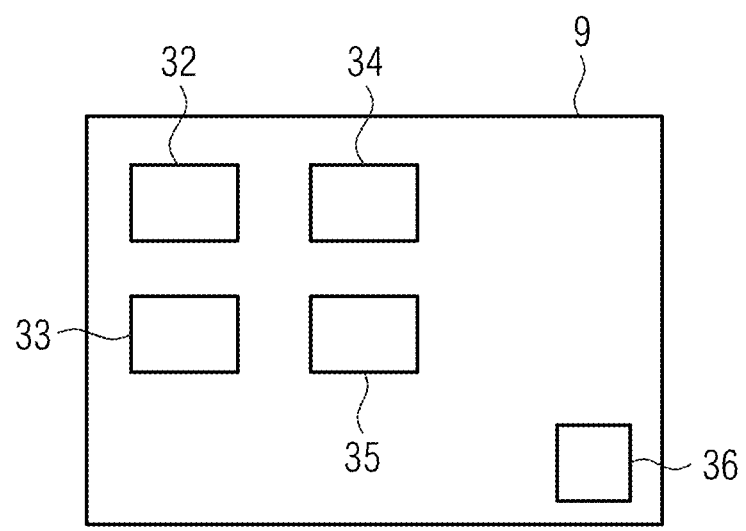
FIG. 6 shows the functional layout of a control facility of the x-ray facility.

Finally, FIG. 6 shows in this regard the functional layout of the control facility 9. Said facility, as well as usual functional units not shown here such as a recording unit, first of all has a determination unit 32, in which the discrepancy information is determined in accordance with step S1. For this purpose, the determination unit 32 can interact with an optional temperature model unit 33, which evaluates the power curve and provides estimated current temperatures.

In a discrepancy model unit 34 the discrepancy model can be applied in accordance with step S2. Finally, in a compensation unit 35, the corresponding correction measures are carried out in accordance with step S3.

The control facility 9 also additionally has a memory means 36, in which for example the temperature model and the discrepancy model can be held.

It should be noted once again at this point that preferably the control facility can directly implement the correction measures automatically. However exemplary embodiments are also naturally conceivable, in which these are first offered for confirmation to the user as a possible correction.

Although the invention has been illustrated and described in greater detail by one or more example embodiments, the invention is not restricted by the disclosed examples and other variations can be derived herefrom by the person skilled in the art without departing from the scope of protection of the invention.

Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative used descriptors herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments using may be implemented hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals s capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible language), markup (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for operating an x-ray facility, having an x-ray emitter arrangement with an x-ray emitter for sending out an x-ray field for examination of an examination object and an x-ray detector to receive of x-ray radiation of the x-ray field, wherein the x-ray emitter arrangement includes
   a mono tank for the x-ray emitter with a housing, in which a radiation exit window for the x-ray radiation generated by the x-ray emitter is arranged, and
   a beam-forming facility configured to set a desired extent and position of the x-ray field, the method comprising:
   determining, via a control facility of the x-ray facility, discrepancy information, the discrepancy information describing a discrepancy between a current extent and position of the x-ray field and the desired position and extent of the x-ray field, the discrepancy being caused by temperature conditions in the x-ray emitter arrangement, and
   activating the beam-forming facility based on the discrepancy information to at least partly compensate for the discrepancy,
   wherein at least one of
      an x-ray tube with a rotary anode arranged rotatably via a carrier arrangement in a vacuum is used as the x-ray emitter and the determining includes measuring at least one part of the discrepancy information via at least one temperature sensor of the x-ray emitter arrangement, or
      at least one part of the discrepancy information describes a power of the x-ray emitter.

2. The method of claim 1, wherein the x-ray tube with the rotary anode arranged rotatably via the carrier arrangement in the vacuum is used as the x-ray emitter.

3. The method of claim 2, wherein the at least one temperature sensor measures at least one of a temperature of the rotary anode or a temperature of the carrier arrangement.

4. The method of claim 1, wherein the at least one part of the discrepancy information describes the power of the x-ray emitter.

5. The method of claim 4, wherein the determining determines a current temperature of the x-ray emitter as the discrepancy information, and the determining a current temperature of the x-ray emitter includes using a temperature model describing heating up and cooling down behaviors of the x-ray emitter.

6. The method of claim 1, wherein the discrepancy information is used as input data for a discrepancy model delivering as output data at least one correction measure.

7. The method of claim 6, wherein at least one parameter of the discrepancy model is determined in a calibration process, the calibration process including measuring discrepancies for various thermal states of the x-ray emitter arrangement described by respective discrepancy information.

8. The method of claim 7, wherein at least one of
   the x-ray detector is used for the calibration process, or
   at least one measured position of a diaphragm of the beam-forming facility is compared with a required position in accordance with the activating.

9. The method of claim 6, further comprising at least one of:
   using at least one measurement facility on one side of the x-ray detector adjoining said detector update the discrepancy model during an examination operation; or
   using the x-ray detector for determining a location of a delimitation of the x-ray field for an examination object not covering the entire x-ray detector.

10. The method of claim 9, wherein at least one part of the discrepancy information is measured as a discrepancy between a location of a delimitation of the x-ray field and a required location in accordance with the desired extent and position of the x-ray field via the x-ray detector or by the at least one measurement facility on one side of the x-ray detector and adjoining the x-ray detector.

11. The method of claim 1, wherein a mammography facility is the x-ray facility, in which the beam-forming facility has a front diaphragm, arranged facing towards a patient and a rear diaphragm arranged facing away from the patient, and at least the position of the front diaphragm is adjusted to compensate for the discrepancy by activation of the beam-forming facility.

12. An x-ray facility comprising:
   an x-ray emitter arrangement with an x-ray emitter for sending out an x-ray field for examination of an examination object and an x-ray detector for receipt of x-ray radiation of the x-ray field, wherein the x-ray emitter arrangement includes,
      a mono tank for the x-ray emitter with a housing, in which a radiation exit window for the x-ray radiation generated by the x-ray emitter is arranged, and
      a beam-forming facility configured to set a desired extent and position of the x-ray field; and
   a control facility including,
      a determination unit configured to determine discrepancy information between a current extent and position of the x-ray field and the desired position and extent of the x-ray field, the discrepancy being caused by temperature conditions in the x-ray emitter arrangement, and
      a compensation unit configured to activate of the beam-forming facility to at least partly compensate for the discrepancy depending on the discrepancy information,
   wherein at least one of
      an x-ray tube with a rotary anode arranged rotatably via a carrier arrangement in a vacuum is used as the x-ray emitter and the determination unit is configured to measure at least one part of the discrepancy information via at least one temperature sensor of the x-ray emitter arrangement; or
      at least one part of the discrepancy information describes power of the x-ray emitter.

13. A non-transitory computer computer-readable medium storing instructions that, when executed on a control facility of an x-ray facility, causes the control facility to perform the method of claim 1.

14. The method of claim 3, wherein the at least one temperature sensor is an infrared sensor.

15. The method of claim 5, wherein the determining the current temperature includes determining at least one of a temperature of a rotary anode or a temperature of a carrier arrangement for the rotary anode.

16. The method of claim 1, wherein at least one temperature sensor measures at least one of a temperature of a rotary anode or a temperature of a carrier arrangement.

\* \* \* \* \*